(12) United States Patent
Li et al.

(10) Patent No.: US 9,194,840 B2
(45) Date of Patent: Nov. 24, 2015

(54) SENSOR ARRAYS AND METHODS FOR MAKING SAME

(75) Inventors: Shifeng Li, Fremont, CA (US); James Bustillo, Castro Valley, CA (US); Wolfgang Hinz, Killingworth, CT (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/354,088

(22) Filed: Jan. 19, 2012

(65) Prior Publication Data

US 2013/0189790 A1   Jul. 25, 2013

(51) Int. Cl.
*G01N 27/27* (2006.01)
*G01N 27/26* (2006.01)
*G01N 27/403* (2006.01)
*B01L 3/00* (2006.01)
*G01N 27/414* (2006.01)

(52) U.S. Cl.
CPC .......... *G01N 27/4145* (2013.01); *B01L 3/5027* (2013.01); *G01N 27/27* (2013.01); *B01L 2200/0668* (2013.01); *B01L 2200/12* (2013.01); *B01L 2300/0636* (2013.01); *B01L 2300/0645* (2013.01); *B01L 2300/0819* (2013.01); *B01L 2300/0877* (2013.01); *B01L 2300/0893* (2013.01); *G01N 27/26* (2013.01); *Y10T 436/14* (2015.01); *Y10T 436/142222* (2015.01); *Y10T 436/143333* (2015.01)

(58) Field of Classification Search
CPC ... G01N 27/00; G01N 27/27; G01N 27/4145; H05K 13/00; B01L 3/5027; Y10T 436/143333; Y10T 436/142222; Y10T 436/14; Y10T 436/00

USPC ................................................ 436/94, 93, 91
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis et al. |
| 4,800,159 | A | 1/1989 | Mullis et al. |
| 4,965,188 | A | 10/1990 | Mullis et al. |
| 5,112,456 | A | 5/1992 | Worrell et al. |
| 5,126,022 | A | 6/1992 | Soane et al. |

(Continued)

FOREIGN PATENT DOCUMENTS

| | | |
|---|---|---|
| GB | 2461127 | 12/2009 |
| JP | 4262799 | 9/2004 |

(Continued)

OTHER PUBLICATIONS

Allen, Phillip E. et al., "CMOS Analog Circuit Design, Second Edition", Oxford University Press, 2002.

(Continued)

*Primary Examiner* — Christine T Mui

(57) ABSTRACT

A system includes a sensor including a sensor pad and includes a well wall structure defining a well operatively connected to the sensor pad. The sensor pad is associated with a lower surface of the well. The well wall structure defines an upper surface and a wall surface extending between the upper surface and the lower surface. The upper surface is defined by an upper buffer material having an intrinsic buffer capacity of at least $2 \times 10^{17}$ groups/m². The wall surface is defined by a wall material having an intrinsic buffer capacity of not greater than $1.7 \times 10^{17}$ groups/m².

24 Claims, 13 Drawing Sheets

(56) References Cited

U.S. PATENT DOCUMENTS

| | | | |
|---|---|---|---|
| 5,210,015 | A | 5/1993 | Gelfand et al. |
| 5,399,491 | A | 3/1995 | Kacian et al. |
| 5,498,392 | A | 3/1996 | Wilding et al. |
| 5,587,128 | A | 12/1996 | Wilding et al. |
| 5,854,033 | A | 12/1998 | Lizardi |
| 5,858,195 | A | 1/1999 | Ramsey |
| 6,001,229 | A | 12/1999 | Ramsey |
| 6,010,607 | A | 1/2000 | Ramsey |
| 6,033,546 | A | 3/2000 | Ramsey |
| 6,054,034 | A | 4/2000 | Soane et al. |
| 6,174,670 | B1 | 1/2001 | Wittwer et al. |
| 6,399,952 | B1 | 6/2002 | Maher et al. |
| 6,613,525 | B2 | 9/2003 | Nelson et al. |
| 6,960,437 | B2 | 11/2005 | Enzelberger et al. |
| 7,049,645 | B2 | 5/2006 | Sawada et al. |
| 7,190,026 | B2 | 3/2007 | Lotfi et al. |
| 7,462,512 | B2 | 12/2008 | Levon et al. |
| 7,535,232 | B2 | 5/2009 | Barbaro et al. |
| 8,592,153 | B1 * | 11/2013 | Bustillo et al. ............ 435/6.1 |
| 2003/0203405 | A1 | 10/2003 | Carlson |
| 2006/0147983 | A1 | 7/2006 | O'uchi |
| 2007/0059741 | A1 | 3/2007 | Kamahori et al. |
| 2007/0207471 | A1 | 9/2007 | Osaka et al. |
| 2008/0166727 | A1 | 7/2008 | Esfandyarpour et al. |
| 2008/0286762 | A1 | 11/2008 | Miyahara et al. |
| 2008/0286767 | A1 | 11/2008 | Miyahara et al. |
| 2009/0127589 | A1 * | 5/2009 | Rothberg et al. ............ 257/253 |
| 2010/0035071 | A1 | 2/2010 | Nishimi et al. |
| 2010/0052080 | A1 | 3/2010 | Garcia-Tello et al. |
| 2010/0137143 | A1 | 6/2010 | Rothberg et al. |
| 2010/0188073 | A1 | 7/2010 | Rothberg et al. |
| 2010/0300895 | A1 | 12/2010 | Nobile et al. |
| 2011/0281741 | A1 * | 11/2011 | Rothberg et al. ............ 506/7 |
| 2012/0001235 | A1 | 1/2012 | Fife |
| 2012/0045368 | A1 * | 2/2012 | Hinz et al. ............ 422/69 |

FOREIGN PATENT DOCUMENTS

| | | |
|---|---|---|
| WO | 9919717 | 4/1999 |
| WO | 0224322 | 3/2002 |
| WO | 2010/020675 | 2/2010 |

OTHER PUBLICATIONS

Anderson, E. et al., "A system for multiplexed direct electrical detection of DNA synthesis", Sensors and Actuators B Chem., vol. 129, 2008, pp. 79-86.

Baker, R J., "CMOS Circuit Design, Layout, and Simulation", Wiley IEEE Press, 2008.

Barbaro, M. et al., "Fully electronic DNA hybridization detection by a standard CMOS biochip", Sensors and Actuators B Chemical, vol. 118, 2006, pp. 41-46.

Bard, Allen et al., "Electrochemical Methods: Fundamentals and Applications", Wiley, 2001.

Cao, Guozhong, "Nanostructures & Nanomaterials: Synthesis, Properties & Applications", Imperial College Press, 2004.

Dieffenbach, Carl (Ed) et al., "PCR Primer: A Laboratory Manual, Second Edition", Cold Spring Harbor Laboratory Press, 2003.

Doering, Robert (Ed) et al., "Handbook of Semiconductor Manufacturing Technology, Second Edition", CRC Press, 2007.

Elwenspoek, M et al., "Silicon Micromachining", Cambridge University Press, 2004.

Hammond, P. et al., "Design of a Single-Chip pH Sensor Using a Conventional 0.6—μm CMOS Process", IEEE Sensors Journal, vol. 4(6), 2004, pp. 706-712.

Heer, F et al., "Single-chip microelectronic system to interface with living cells", Biosensors and Bioelectronics, vol. 22, 2007, pp. 2546-2553.

Hizawa, T et al., "Fabrication of a two-dimensional pH image sensor using a charge transfer technique", Sensors and Actuators B Chemical, vol. 117, 2006, pp. 509-515.

Hughes, R C. et al., "Chemical Microsensors", Science, vol. 254, 1991, pp. 74-80.

Krause, M. et al., "Extended gate electrode arrays for extracellular signal recordings", Sensors and Actuators B, vol. 70, 2000, pp. 101-107.

Levinson, Harry, "Principles of Lithography, Second Edition", SPIE Press Monograph vol. PM146, 2005.

Martinoia, S. et al., "Development of ISFET Array-Based Microsystems for Bioelectrochemical measurements of cell populations", Biosensors & Bioelectronics, vol. 16, 2001, pp. 1043-1050.

Milgrew, M. et al., "A large transistor based sensor array chip for direct extracellular imaging", Sensors and Actuators B Chemical, vol. 111-112, 2005, pp. 347-353.

Milgrew, M. et al., "The development of scalable sensor arrays using standard CMOS technology", Sensors and Actuators B, vol. 103, 2004, pp. 37-42.

Mir, Monica et al., "Integrated electrochemical DNA biosensors for lab-on-a-chip devices", Electrophoresis, vol. 30, 2009, 3386-3397.

Ohmori, Kazuyuki et al., "Performance of Cu Dual-Damascene Interconnects Using a Thin Ti-Based Self-Formed Barrier Layer for 28nm Node and Beyond", Japanese Journal of Applied Physics, vol. 49(05FD01), 2010, pp. 1-4.

PCT/US2011/048268 International Preliminary Report on Patentability dated Feb. 19, 2013.

PCT/US2011/48268 International Search Report and Written Opinion dated Jan. 6, 2012.

PCT/US2013/021622, "International Search Report of the International Searching Authority and Written Opinion" dated May 14, 2013.

Saliterman, Steven, "Fundamentals of BioMEMS and Medical Microdevices", SPIE Press, Wiley-Interscience, 2006.

Sawyer, Donald T. et al., "Electrochemistry for Chemists, Second Edition", Wiley-Interscience, 1995.

Sia, S et al., "Microfluidic devices fabricated in poly(dimethylsiloxane) for biological studies", Electrophoresis, 24, 2003, pp. 3563-3576.

Trojanowicz, Marek, "Recent developments in electrochemical flow detections—A review Part I. Flow analysis and capillary electrophoresis", Analytica Chimica Acta, vol. 653, 2009, pp. 36-58.

Unger, M et al., "Monolithic Microfabricated Valves and Pumps by Multilayer Soft Lithography", Science, 288, 2000, pp. 113-116.

Veendrick, Harry, "Deep-Submicron CMOS ICs: From Basics to ASICs", Kluwer Academic Publishing, 1998.

Xu, Xiaoli et al., "Integration of electrochemistry in micro-total analysis systems for biochemical assays: Recent developements", Talanta, vol. 80, 2009, pp. 8-18.

Yeow, T.C.W. et al., "A very large integrated pH-ISFET sensor array chip compatible with standard CMOS processes", Sensor and Actuators B, vol. 44, 1997, pp. 434-440.

* cited by examiner

SENSOR ARRAYS AND METHODS FOR MAKING SAME

FIELD OF THE DISCLOSURE

This disclosure, in general, relates to sensor arrays and methods for making same.

BACKGROUND

Electronic sensor arrays are finding increased use for detecting analytes in fluids, such as gases or liquids. In particular, arrays of sensors based on field effect transistors are finding use in detecting ionic components, such as various cations, anions or pH. Such sensors are often referred to as ion-sensitive field effect transistors or ISFETs.

Recently, such sensor arrays have found use in sequencing polynucleotides. Nucleotide addition results in the release of ionic species that influence the pH in a local environment. Sensors of the sensor arrays are used to detect changes in pH in the local environment resulting from the nucleotide addition. However, the pH of the local environment can be influenced by adjacent environments, referred to as crosstalk, and can be influenced by the interaction of various materials with hydrogen ions, leading to lower accuracy and less sensitivity to the changes caused by nucleotide addition.

As such, an improved sensor array would be desirable.

SUMMARY

In a first aspect, a system includes a sensor including a sensor pad and a well wall structure defining a well operatively connected to the sensor pad. The sensor pad is associated with a lower surface of the well. The well wall structure defines an upper surface and a wall surface extending between the upper surface and the lower surface. The upper surface is defined by an upper buffer material having an intrinsic buffer capacity of at least $2\times10^{17}$ groups/m$^2$. The wall surface is defined by a wall material having an intrinsic buffer capacity of not greater than $1.7\times10^{17}$ groups/m$^2$.

In a second aspect, a method of forming a sensor system includes forming a structural layer over a sensor device. The sensor device includes a sensor pad. The structural layer includes a structural material having an intrinsic buffer capacity of not greater than $1.7\times10^{17}$ groups/m$^2$. The method further includes forming a buffer layer over the structural layer. The buffer layer includes a buffer material having an intrinsic buffer capacity of at least $2\times10^{17}$ groups/m$^2$. The method also includes etching the buffer layer and the structural layer to define a well operatively connected to the sensor pad.

In a third aspect, a method of sequencing a polynucleotide includes applying a particle comprising a plurality of copies of a polynucleotide to a well of a system of the first aspect, exposing the particle to an aqueous solution including a nucleotide, and measuring a response of the device to the exposing.

In a fourth aspect, a system includes a sensor device including a sensor pad and a well wall structure defining a well in operative connection with the sensor pad. A lower surface of the well is defined over the sensor pad. The well wall structure has an upper surface and a wall surface extending between the upper surface and the lower surface. The system includes a passivation film disposed over the upper surface, the wall surface and the lower surface and an isolation film disposed over the passivation film opposite the well wall structure and extending substantially parallel to and at least along a portion of the wall surface. The passivation layer is exposed at least along a portion of the upper surface and at least along a portion of the lower surface.

In a fifth aspect, a method of forming a sensor system includes forming a structural layer over a sensor device, the sensor device including a sensor pad and etching the structural layer to define a well operatively connected to the sensor pad. A lower surface of the well is defined over the sensor pad. The structurally layer has an upper surface and a wall surface extending between the upper surface and the lower surface. The method includes forming a passivation film over the structural layer. The passivation film extends along at least a portion of the upper surface and extends over the wall surface and the lower surface. The method further includes forming an isolation film over the passivation film and etching the isolation film to expose the passivation film along at least the portion of the upper surface and at least a portion of the lower surface.

In a sixth aspect, a method of sequencing a polynucleotide includes applying a particle comprising a plurality of copies of a polynucleotide to a well of a system of the fourth aspect, exposing the particle to an aqueous solution including a nucleotide, and measuring a response of the device to the exposing.

In a seventh aspect, a system includes a sensor device including a sensor pad and a well wall structure defining a well in operative connection with the sensor pad. A lower surface of the well is defined over the sensor pad. The well wall structure has an upper surface, and a wall surface extends between the upper surface and the lower surface. A metal layer is disposed over the well wall structure and extends along the upper surface and the wall surface.

In an eighth aspect, a method of forming a sensor system includes forming a structural layer over a sensor device, the sensor device including a sensor pad, and etching the structural layer to form a trench defining a well post over the sensor pad and a well wall structure opposite the first structure, the well post extending vertically higher than the well wall structure. The method further includes depositing a metal layer into the trench and over the well post and the well wall structure, exposing the well post, and etching to remove the well post.

In a ninth aspect, a method of forming a sensor system includes forming a structural layer over a sensor device, the sensor device including a sensor pad, etching the structural layer to form a well post over the sensor pad, depositing a metal layer to surround the well post, and etching to remove the well post.

In a tenth aspect, a method of sequencing a polynucleotide includes applying a particle comprising a plurality of copies of a polynucleotide to a well of a system of the seventh aspect, exposing the particle to an aqueous solution including a nucleotide, and measuring a response of the device to the exposing.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, a sensor system includes a sensor having a sensor pad and a well wall structure defining a well in operative connection with the sensor pad. Optionally, a passivation layer is disposed over the sensor pad and defines a lower surface of the well. The well wall structure defines an upper surface and a wall surface extending between the upper surface and the lower surface of the well. In particular, the well wall surface may extend substantially vertically, defined as extending in a direction having component that is normal to a surface defined by the sensor pad. In a particular example, the upper surface is formed of a buffer material having an intrinsic buffer capacity of at least $2 \times 10^{17}$ groups/m$^2$. The wall surface is formed of a wall material having an intrinsic buffer capacity of not greater than $1.7 \times 10^{17}$ groups/m$^2$. Optionally, the lower surface of the well may be formed of a material having an intrinsic buffer capacity of at least $2 \times 10^{17}$ groups/m$^2$. In particular, such a system can reduce the influence of an adjacent wells on the local environment of the well and can improve sensitivity of the sensor.

Figure 1:
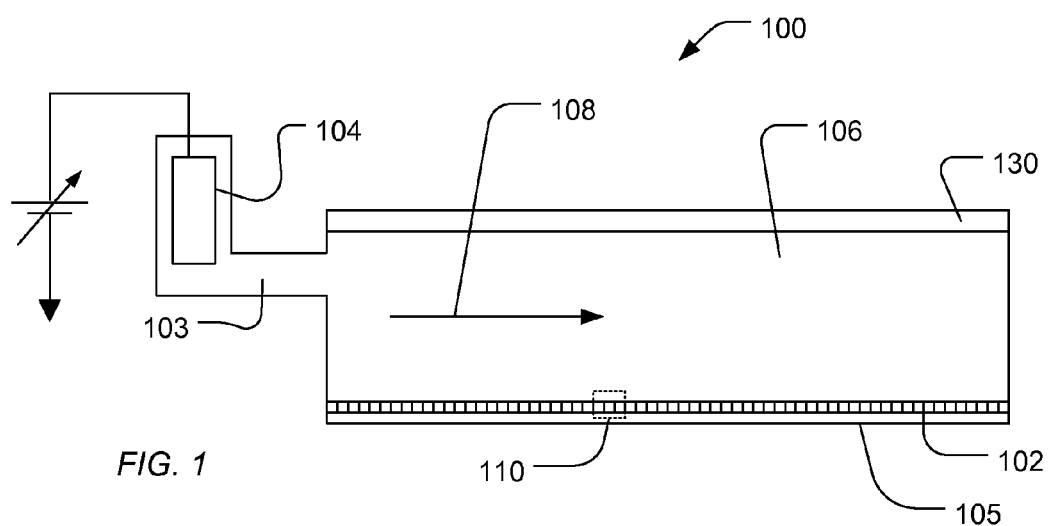
FIG. 1 includes an illustration of an exemplary system including a sensor array.

In a particular embodiment, a sequencing system includes a flow cell in which a sensory array is disposed, includes communication circuitry in electronic communication with the sensory array, and includes containers and fluid controls in fluidic communication with the flow cell. In an example, FIG. 1 illustrates an expanded and cross-sectional view of a flow cell 100 and illustrates a portion of a flow chamber 106. A reagent flow 108 flows across a surface of a microwell array 102, in which the reagent flow 108 flows over the open ends of microwells of the microwell array 102. The microwell array 102 and a sensor array 105 together may form an integrated unit forming a lower wall (or floor) of flow cell 100. A reference electrode 104 may be fluidly coupled to flow chamber 106. Further, a flow cell cover 130 encapsulates flow chamber 106 to contain reagent flow 108 within a confined region.

Figure 2:
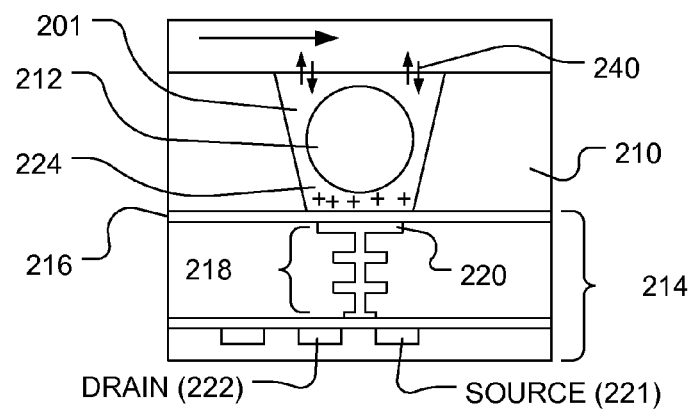
FIG. 2 includes an illustration of an exemplary sensor and associated well.

FIG. 2 illustrates an expanded view of a microwell 201 and a sensor 214, as illustrated at 110 of FIG. 1. The volume, shape, aspect ratio (such as base width-to-well depth ratio), and other dimensional characteristics of the microwells may be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 separated from the microwell interior by a passivation layer 216. The sensor 214 can be responsive to (and generate an output signal related to) the amount of a charge 224 present on passivation layer 216 opposite the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, wash solutions, and other reagents may move in and out of the microwells by a diffusion mechanism 240.

In an embodiment, reactions carried out in the microwell 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, then multiple copies of the same analyte may be analyzed in the microwell 201 at the same time in order to increase the output signal generated. In an embodiment, multiple copies of an analyte may be attached to a solid phase support 212, either before or after deposition into the microwell 201. The solid phase support 212 may be microparticles, nanoparticles, beads, solid or porous comprising gels, or the like. For simplicity and ease of explanation, solid phase support 212 is also referred herein as a particle. For a nucleic acid analyte, multiple, connected copies may be made by rolling circle amplification (RCA), exponential RCA, or like techniques, to produce an amplicon without the need of a solid support.

Figure 3:
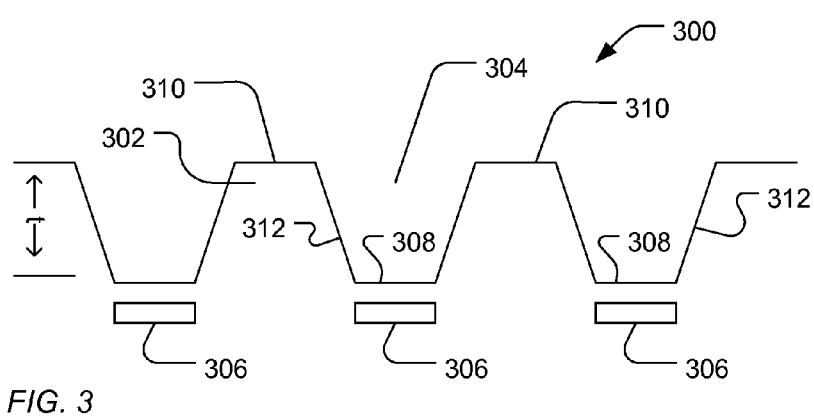
FIG. 3 includes an illustration of an exemplary well structure.

In a particular example, FIG. 3 illustrates a system 300 including a well wall structure 302 defining wells 304. The wells 304 are in operative connection with sensor pads 306 of sensors. In particular, a lower surface 308 of the well 304 is defined over at least a portion of the sensor pad 306. The well wall structure 302 defines an upper surface 310 and defines a wall surface 312 extending between the upper surface 310 and the lower surface 308.

The well wall structure 302 can be formed of one or more layers of material. In an example, the well wall structure 302 can have a thickness extending from the lower surface 308 to the upper surface 310 in a range of 0.3 micrometers to 10 micrometers, such as a range of 0.5 micrometers to 6 micrometers. The wells 304 can have a characteristic diameter, defined as the square root of 4 times the cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers.

In a particular example, the upper surface 310 is defined by an upper buffer material having an intrinsic buffer capacity of at least $2 \times 10^{17}$ groups/m$^2$. Intrinsic buffer capacity is defined as the surface density of hydroxyl groups on a surface of a material measured at a pH of 7. Such a buffer material is referred to as a high intrinsic buffer capacity material. For example, the upper buffer material can have an intrinsic buffer capacity of at least $4 \times 10^{17}$ groups/m$^2$, such as at least $8 \times 10^{17}$ groups/m$^2$, at least $1 \times 10^{18}$ groups/m$^2$, or even at least $2 \times 10^{18}$ groups/m$^2$. In an example, the upper buffer material has an intrinsic buffer capacity of not greater than $1 \times 10^{21}$ groups/m$^2$.

In particular, the upper buffer material is a high intrinsic buffer capacity material that can include an inorganic material, such as a ceramic material. For example, a ceramic material can include an oxide of aluminum, hafnium, tantalum, zirconium, or any combination thereof. In an example, the ceramic material can include an oxide of tantalum. In another example, the ceramic material includes an oxide of zirconium. In a further example, the upper surface 310 can be coated with a pH buffering coating. An exemplary pH buffering coating can include a functional group, such as phosphate, phosphonate, catechol, nitrocatechol, boronate, phenylboronate, imidazole, silanol, another pH-sensing group, or a combination thereof.

The wall surface 312 is defined by a wall material having a low intrinsic buffer capacity, such as not greater than $1.7 \times 10^{17}$ groups/m$^2$. For example, the intrinsic buffer capacity of the wall material can be not greater than $1 \times 10^{17}$ groups/m$^2$, such as not greater than $5 \times 10^{16}$ groups/m$^2$, not greater than $2\times10^{16}$ groups/m$^2$, not greater than $1\times10^{16}$ groups/m$^2$, or even not greater than $5\times10^{15}$ groups/m$^2$.

In an example, the wall material includes a low intrinsic buffer capacity material that can include an inorganic material, such as a ceramic material. An exemplary ceramic material can include a nitride of silica, titanium, or a combination thereof. In another example, the ceramic material includes an oxide of silicon. In an additional example, the ceramic material can include silicon oxynitride. In a further example, the inorganic material can include a metal. For example, the metal can include aluminum, copper, nickel, titanium, silver, gold, platinum, or a combination thereof. In particular, the metal can include copper.

Alternatively, the wall material can include an organic material, such as a polymeric material. An exemplary polymeric material includes a polymer having an aromatic group in its backbone. For example, the polymer can be a poly (xylylene), such as a poly(p-xylylene), optionally including functionalize p-xylylenes, such as halogenated p-xylylenes. In another example, the polymeric material includes a fluoropolymer. An exemplary fluoropolymer includes polytetrafluoroethylene (PTFE), polyvinylidene fluoride (PVDF), polyvinyl fluoride (PVF), fluorinated ethylene propylene (FEP) copolymer, ethylene chlorotrifluoroethylene (ECTFE) copolymer, a copolymer of tetrafluoroethylene, hexafluoropropylene, and vinylidene fluoride (THV), a copolymer of tetrafluoroethylene and perfluoro methylvinylether (PFA or MFA), a fluoropolymer having a fluorinated oxolane in its backbone, perfluoroether, or any combination thereof. In particular, the fluoropolymer can be a fluoropolymer having fluorinated oxolane in its backbone, for example, Cytop. Further, the polymer coating can be amorphous, exhibiting little or no crystallinity.

In a further example, the wall material can include a low buffer capacity coating. In particular, the low buffer capacity coating can include a silane component. In an embodiment, the silane component can be R—[(CH2)n]—Si—[X1 X2 X3] where R is an organofunctional group, [(CH2)n] is a hydrocarbon linker (n=1 to 20), Si is a silicon atom, and X1, X2, or X3 comprise one or more independent hydrolysable groups, including alkoxy or halogen groups. In another embodiment, the silane component can be R—[(C2H4O)n]—Si—[X1 X2 X3] where R is an organofunctional group, [(C2H4O)n] (n=1 to 100) is a polyether linker, Si is a silicon atom, and X1, X2, or X3 comprise one or more hydrolysable groups, including alkoxy or halogen groups. In either of the embodiments, organofunctional groups R can include methyl, methylene, phenyl, benzyl, anilino, amino, amide, hydroxyl, aldehyde, alkoxy, halo, mercapto, carboxy, acyl, vinyl, allyl, styryl, epoxy, isocyanato, glycidoxy, acryloxy, or a combination thereof. Examples of the silane component can include N-((6-aminohexyl)aminomethyltriethoxysilane, (mercaptomethyl) methyldiethoxysilane, chloromethyltriethoxysilane, (isocyanatomethyl)methyldimethoxysilane, N-phenylaminomethyltriethoxysilane, triethoxysilylundecanal, 11-mercaptoundecyltrimethoxysilane, 10-undecenyltrimethoxysilane, N-(2-aminoethyl)-11-aminoundecyltrimethoxysilane, 11-bromoundecyltrimethoxysilane, n-octyltrimethoxysilane, 2-[methoxy(polyethyleneoxy)propyl]trimethoxysilane, 3-methoxypropyltrimethoxysilane, methoxytriethyleneoxypropyltrisilane, methoxy silane, methoxyethoxyundecyltrichlorosilane, 2-[methoxy(polyethyleneoxy)propyl]-trichlorosilane, or a combination thereof.

The lower surface 308 of the well can be defined by lower buffer material disposed over the sensor pad 306. For example, the lower buffer material can have an intrinsic buffer capacity of at least $2\times10^{17}$ groups/m$^2$, such as at least $4\times10^{17}$ groups/m$^2$, at least $8\times10^{17}$ groups/m$^2$, at least $1\times10^{18}$ groups/m$^2$, or even at least $2\times10^{18}$ groups/m$^2$. In a particular example, the lower buffer material has an intrinsic buffer capacity of not greater than $1\times10^{21}$ groups/m$^2$. In an example, the lower buffer material can include an inorganic material, such as a ceramic material. For example, a ceramic material can include an oxide of aluminum, hafnium, tantalum, zirconium, or any combination thereof. In particular, the ceramic material can include an oxide of tantalum. In another example, the ceramic material includes an oxide of zirconium. In a further example, the lower surface 308 can be coated with a pH sensitive coating. Exemplary pH sensitive coatings can include a functional group, such as phosphate, phosphonate, catechol, nitrocatechol, boronate, phenylboronate, imidazole, silanol, another pH-sensing group, or a combination thereof. In a further example, the lower buffer material can be the same as the upper buffer material. For example, the lower buffer material and the upper buffer material can be formed as a single layer over the well wall structure 302. Alternatively, the upper buffer material and lower buffer material can be formed as separate layers and can be different.

Figure 4:
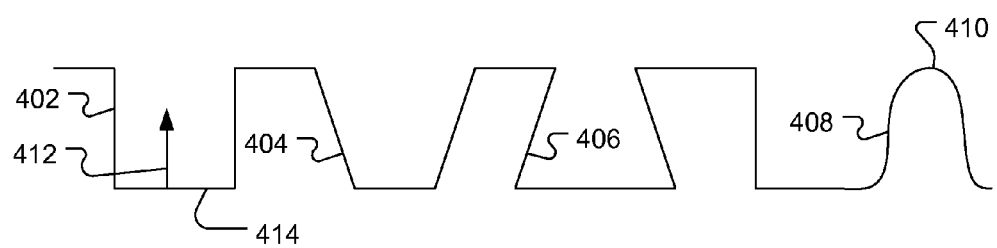
FIG. 4 includes cross-sectional illustrations of exemplary well configurations.

In particular, the wall surface 312 extends substantially vertically, defined as extending in a direction having a component that is normal to the surface defined by the sensor pad. For example, as illustrated in FIG. 4, a well wall 402 can extend vertically, being parallel to a normal component 412 of a surface 414 defined by a sensor pad. In another example, the wall surface 404 extends substantially vertically, in an outward direction away from the sensor pad, providing a larger opening to the well than the area of the lower surface of the well. As illustrated in FIG. 4, the wall surface 404 extends in a direction having a vertical component parallel to the normal component 412 of the surface 414. In an alternative example, a wall surface 406 extends substantially vertically in an inward direction, providing an opening area that is smaller than an area of the lower surface of the well. The wall surface 406 extends in a direction having a component parallel to the normal component 412 of the surface 414.

While the surfaces 402, 404, or 406 are illustrated by straight lines, some semiconductor or CMOS manufacturing processes can result in structures having nonlinear shapes. In particular, wall surfaces, such as wall surface 408 and upper surfaces, such as upper surface 410, can be arcuate in shape or take various nonlinear forms. While the structures and devices illustrated herewith are depicted as having linear layers, surfaces, or shapes, actual layers, surfaces, or shapes resulting from semiconductor processing may differ to some degree, possibly including nonlinear and arcuate variations of the illustrated embodiment.

Returning to FIG. 3, the well wall structure 302 and the surfaces 310, 312, and 308 can be defined by one or more materials. Specific embodiments are presented below that identify specific material layers. However, it is understood that various materials described above can be substituted for the identified material layers.

In a particular embodiment, a well wall structure includes one or more layers defining the well wall. Such layers can be formed of materials having low intrinsic buffer capacity. In addition, the well wall structure includes a film defining an upper surface of the well wall structure, which is formed of a buffer material having a high intrinsic buffer capacity. Further, a lower surface of the well is defined by a passivation material having high buffer capacity. The passivation material is disposed over a sensor pad. For example, FIG. 9 includes an illustration of an exemplary well wall structure 828 that defines a well 822 over a passivation layer 610 and a sensor pad 608. The passivation layer 610 is exposed to form a lower surface 930 of the well 822. The well wall structure 828 defines a wall surface 824 extending between an upper surface 826 and the lower surface 930. The well wall structure 828 includes one or more layers of low intrinsic buffer capacity material that define the wall surface 824. An additional film 720 defines the upper surface 826 and is formed of a high intrinsic buffer capacity material. In an example, a structure such as that illustrated in FIG. 9 can be formed by a process such as a process illustrated in FIGS. 5-9.

Figure 5:
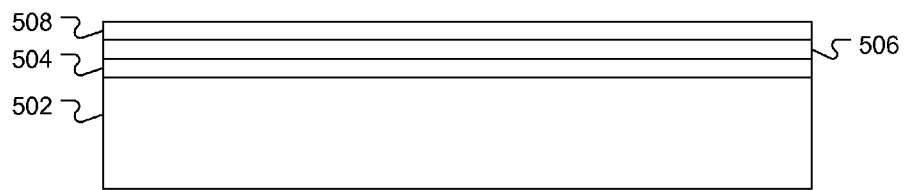
FIG. 5 through FIG. 33 include illustrations of exemplary work pieces during exemplary manufacturing processes.

As illustrated in FIG. 5, a conductive layer 504 is deposited over a CMOS structure 502. The CMOS structure 502 can include a sensor structure to be operatively coupled to a sensory pad. In addition, one or more passivation layers 506 or 508 can be deposited over the conductive layer 504. In an example, the conductive layer 504 is formed by a metal deposition technique, such as atomic layer deposition, sputtering, e-beam evaporation, electrochemical deposition, or a combination thereof. The passivation layers 506 or 508 can be deposited over the conductive layer 504 using atomic layer deposition or other techniques. In particular, the passivation layers 506 or 508 can include an oxide of aluminum, hafnium, tantalum, zirconium, or a combination thereof. In a particular example, the passivation layer 506 includes an oxide of tantalum and the passivation layer 508 includes an oxide of aluminum.

Figure 6:
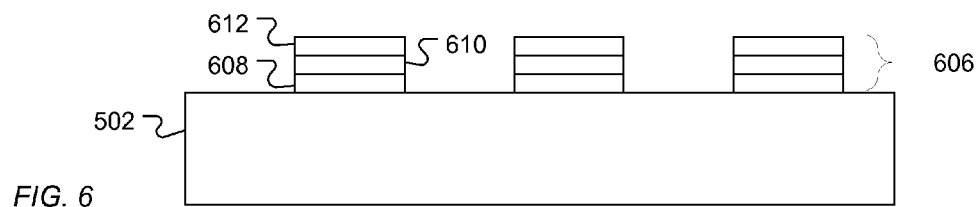

The layers 504, 506, or 508 can be patterned to expose a surface of the CMOS structure 502 and define stack structures 606. For example, as illustrated in FIG. 6, a stack structure 606 including a conductive sensor pad 608 can overlie the CMOS structure 502. In the illustrated example, a layer 610 includes tantalum oxide and a layer 612 includes aluminum oxide. Optionally, an aluminum oxide layer (not illustrated) can be disposed between the sensor pad 608 and the layer 610. Alternatively, the layers 610 or 612 can be formed of zirconium oxide. In an example, each of the layers 610 or 612 can have a thickness in a range of 5 nm to 100 nm, such as a range of 10 nm to 70 nm, a range of 15 nm to 65 nm, or even a range of 20 nm to 50 nm.

Figure 7:
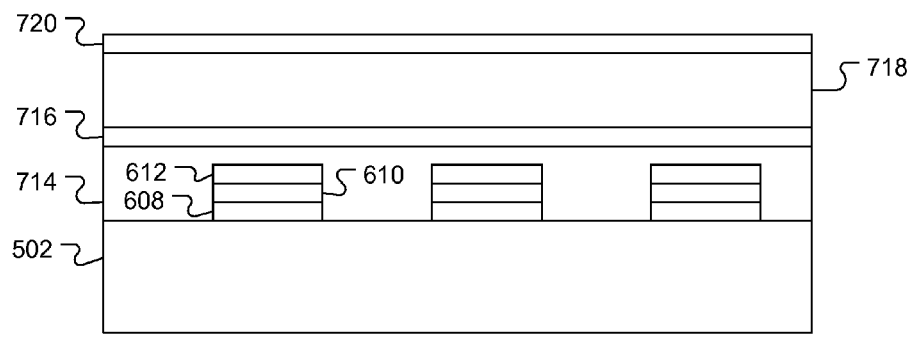

As illustrated in FIG. 7, one or more layers 714, 716, or 718 can be deposited over the CMOS structure 502 and the sensor pad 608. In an example, one or more layers of an oxide of silicon, a nitride of silicon, or TEOS can be deposited to overlie the stack structure 606. In the illustrated example, a layer 714 of silicon oxide is deposited over the CMOS structure 502. A layer 716 of silicon nitride is deposited over the layer 714, and a layer 718 of silicon oxide or TEOS is deposited over the layer 714. In addition, a buffer material layer 720 can be deposited over the layers 714, 716 or 718. The total thickness of the one or more layers 714, 716, 718, or 720 can be in a range of 0.3 micrometers to 10 micrometers, such as a range of 0.5 micrometers to 6 micrometers.

Figure 8:
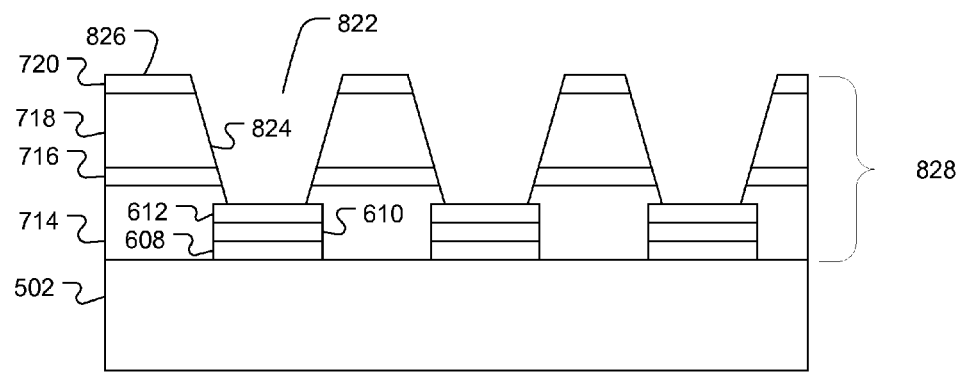

As illustrated in FIG. 8, the layers 714, 716, 718, or 720 can be etched to define a well 822 and a well wall structure 828. In an example, the wells 822 can be exposed using a wet patch, a plasma etch, or a combination thereof. In particular, a fluorinated plasma etch process with endpoint detection can be utilized to form a well that terminates at the aluminum oxide layer 612. In particular, a fluorinated plasma etch using fluorinated species, such as trifluoromethane, tetrafluoromethane, nitrogen fluoride, sulfur hexafluoride, or a combination thereof, can be utilized. As a result, an upper surface 826 is defined by the buffer material of the layer 720. The wall surface 824 is defined by the material of layers 714, 716, or 718, which are formed of low intrinsic buffer capacity materials.

Figure 9:
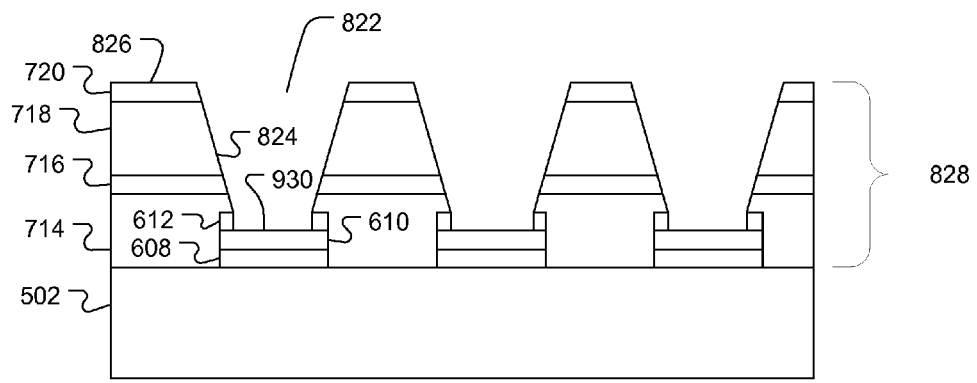

As illustrated in FIG. 9, a wet etch process can be used to remove a portion of the aluminum oxide layer 612 to expose the tantalum oxide layer 610 and to define a lower surface 930 of the well 822. As such, the lower surface of the well is formed of a high intrinsic buffer capacity material, while the wall surface 824 is formed of a low intrinsic buffer capacity material, and the upper surface 826 is formed of a high intrinsic buffer capacity material.

Figure 10:
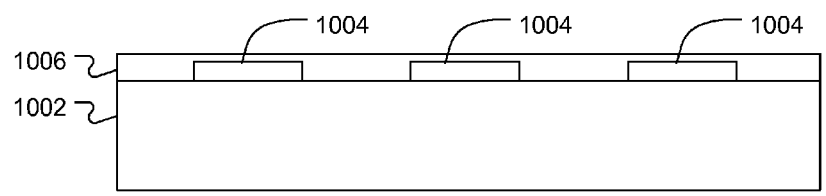

In an alternative process, a similar structure can be formed as illustrated in FIGS. 10-15. For example, as illustrated in FIG. 10, sensor pads 1004 can be formed over a CMOS structure 1002. An insulation material layer 1006 can be deposited over the sensor pads 1004. The insulation material layer 1006 can be formed of an insulation material, such as silicon dioxide, silicon oxynitride, or a combination thereof. In an example, the insulation material layer 1006 has a thickness in a range of 0.3 micrometers to 1.5 micrometers, such as 0.4 micrometers to 1.0 micrometers, or even a range of 0.4 micrometers to 0.7 micrometers.

Figure 11:
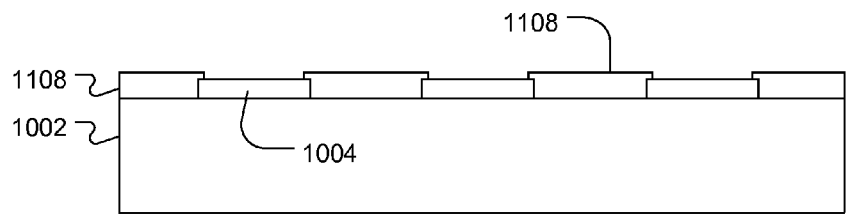

As illustrated in FIG. 11, the insulation layer 1006 can be patterned using lithographic method and can be etched to expose the sensor pads 1004. As a result, insulation structures 1108 are formed between the sensor pads 1004.

Figure 12:
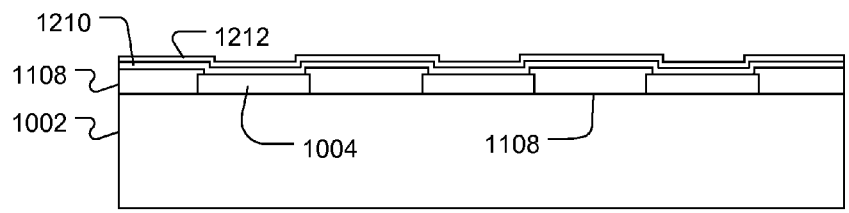

A high intrinsic buffer capacity material can be deposited over the structures 1108 and the sensor pads 1004. For example, as illustrated in FIG. 12, layers of high intrinsic buffer capacity material, such as aluminum oxide, hafnium oxide, tantalum oxide, zirconium oxide or a combination thereof, can be deposited over the structures 1108 and the sensor pads 1004. In particular, a layer 1210 of tantalum oxide can be deposited over the structures 1108 and the sensor pads 1004 and a layer 1212 of aluminum oxide can be deposited over the layer 1210 of tantalum oxide. Optionally, a layer (not illustrated) of aluminum oxide can be deposited between the layer 1210 and the structures 1108 or the sensory pads 1004. In a particular example, the layers 1210 or 1212 can have a thickness in a range of 5 nm to 100 nm, such as a range of 10 nm to 70 nm, a range of 15 nm to 65 nm, or even a range of 20 nm to 50 nm.

Figure 13:
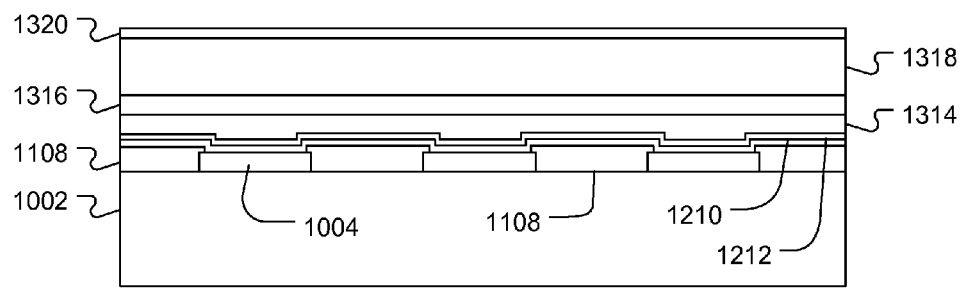

As illustrated in FIG. 13, one or more layers 1314, 1316, or 1318 of low intrinsic buffer capacity material can be deposited over the layers 1210 or 1212. For example, one or more layers silicon oxide, silicon nitride, silicon oxynitride, tetraethoxysilane (TEOS) or a combination thereof can be deposited over the layers 1210 or 1212. Such low intrinsic buffer capacity materials can be deposited using TEOS deposition techniques. Alternatively, chemical vapor deposition can be used to form such layers. In a further alternative, one or more of the layers can be formed of a polymer, such as a polyxylylene or a fluoropolymer.

In the illustrated example, a layer 1314 of silicon dioxide is deposited over the layers 1210 and 1212. A layer 1316 of silicon nitride is deposited over the layer 1314, and a layer 1318 of silicon dioxide is deposited over the layer 1316. Optionally, a high intrinsic buffer capacity material layer 1320 can be deposited over the layer 1318. The total thickness of the layers 1314, 1316, or 1318 can be in a range of 1 µm to 10 µm, such as a range of 2 µm to 7 µm, or even a range of 3 µm to 5 µm. The layer 1320 can have a thickness in a range of 5 nm to 100 nm, such as a range of 10 nm to 70 nm, a range of 15 nm to 65 nm, or even a range of 20 nm to 50 nm.

Figure 14:
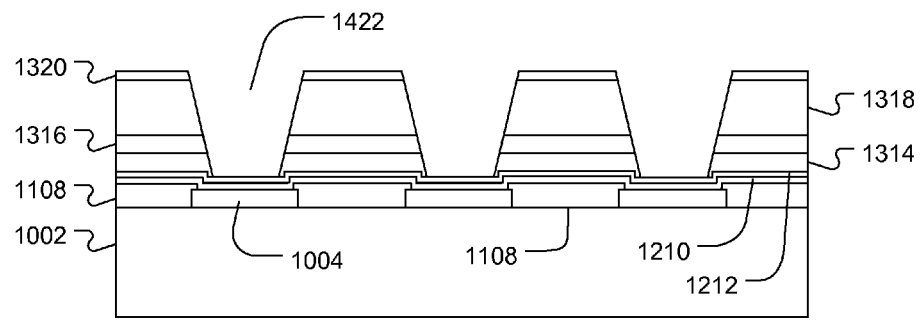

Following patterning, for example, using lithography followed by etching, a well 1422 is opened through layers 1314, 1316, 1318, or 1320, as illustrated in FIG. 14. A wet etch process, plasma etch process, or combination thereof can be used to open the well 1422. In an example, a plasma etch with etch stop detection can be used. In particular, a fluorinated plasma etch using fluorinated species, such as trifluoromethane, tetrafluoromethane, nitrogen fluoride, sulfur hexafluoride, or a combination thereof, can be utilized.

Figure 15:
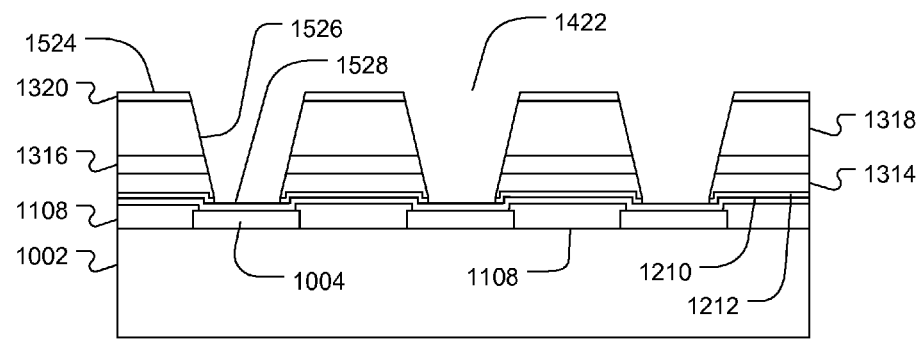

As illustrated in FIG. 15, a wet etch technique can be used to strip the aluminum oxide layer 1212, exposing the tantalum oxide layer 1210 over the sensor pad 1004. As a result, a similar structure is formed as described in relation to FIG. 9 in which an upper surface 1524 includes a high intrinsic buffer capacity material, a wall surface 1526 is formed of low intrinsic buffer capacity materials, and a lower surface 1528 of the well 1422 includes a high intrinsic buffer capacity material.

Figure 16:
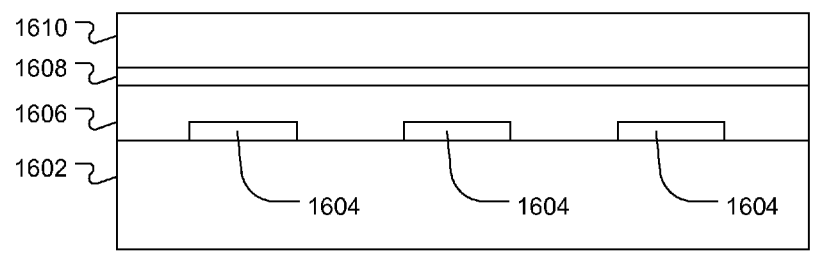

In an alternative example, a high intrinsic buffer capacity material can be deposited in a single layer to form an upper surface of the well wall structure and a lower surface associated with the well. For example, as illustrated in FIG. 16, one or more layers can be deposited over a CMOS structure 1602 and sensor pads 1604. The CMOS structure 1602 includes a portion of the sensor device operatively coupled to the sensor pad 1604. One or more layers (1606, 1608, or 1610) of low buffer capacity material can be deposited over the sensor pads 1604. Exemplary materials include silicon dioxide, silicon nitride, silicon oxynitride, tetraethoxysilane (TEOS) or a combination thereof. In the illustrated example, a layer 1606 of silicon dioxide is deposited over the sensor pads 1604 and the CMOS structure 1602. A layer 1608 of silicon nitride is deposited over the layer 1606, and a layer 1610 of silicon dioxide is deposited over the layer 1608. The layers 1606, 1608, or 1610 can be formed using chemical vapor deposition (CVD), TEOS deposition through plasma enhanced CVD, a hydrolysis method, or a combination thereof. The total thickness of the layers 1606, 1608, or 1610 can be in a range of 0.3 micrometers to 10 micrometers, such as a range of 0.5 micrometers to 6 micrometers.

Figure 17:
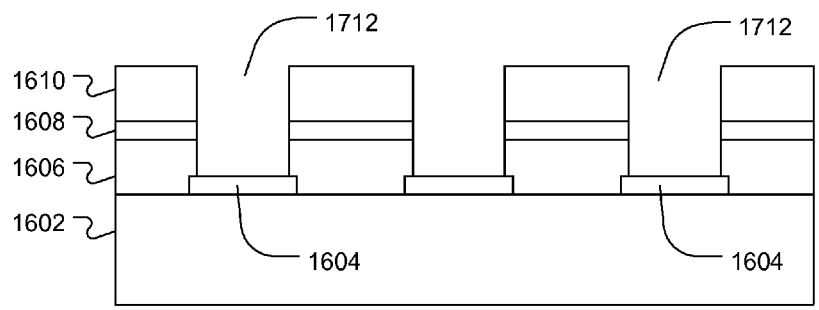

As illustrated in FIG. 17, the layers 1606, 1608, or 1610 can be patterned using lithographic techniques and can be etched to expose the sensor pads 1604, defining wells 1712. For example, etch technique, such as wet etch, plasma etch techniques, or a combination thereof, can be used to open the well 1712. In a particular example, a fluorinated plasma etch using fluorinated species, such as trifluoromethane, tetrafluoromethane, nitrogen fluoride, sulfur hexafluoride, or a combination thereof, can be used.

Figure 18:
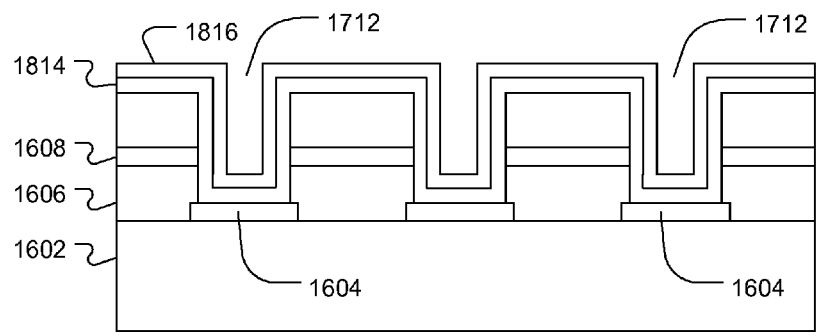

A film 1814 of high intrinsic buffer capacity material can be deposited over the etched layers 1606, 1608, or 1610 and the sensor pad 1604, as illustrated in FIG. 18. For example one or more layers of aluminum oxide, hafnium oxide, tantalum oxide, zirconium oxide, or a combination thereof can be deposited using atomic layer deposition technique. In a particular example, a three layer stack including a layer of aluminum oxide over a layer of tantalum oxide over a further layer of aluminum oxide can be deposited to form the film 1814. The film 1814 can have a total thickness in a range of 20 nm to 500 nm, such as a range of 20 nm to 300 nm, or even a range of 20 nm to 250 nm. In an example in which multiple layers are used to form the film 1814, each of the layers can have a thickness in a range of 10 nm to 100 nm, such as a thickness in a range of 10 nm to 50 nm, or even a range of 10 nm to 30 nm. In a particular embodiment, a three layer stack including 20 nm layers of aluminum oxide, tantalum oxide, and a further layer of aluminum oxide can be deposited using an atomic layer deposition technique.

A further layer of low intrinsic buffer capacity material can be deposited over the film 1814. For example, a layer 1816 including an oxide of silicon can be deposited over the film 1814. Alternatively, the layer 1816 can be formed of nitrides of silicon or other low intrinsic buffer capacity materials. In particular, the layer 1816 has a thickness in a range of 50 nm to 1 micrometer, such as a range of 50 nm to 500 nm, or even a range of 100 nm to 300 nm.

Figure 19:
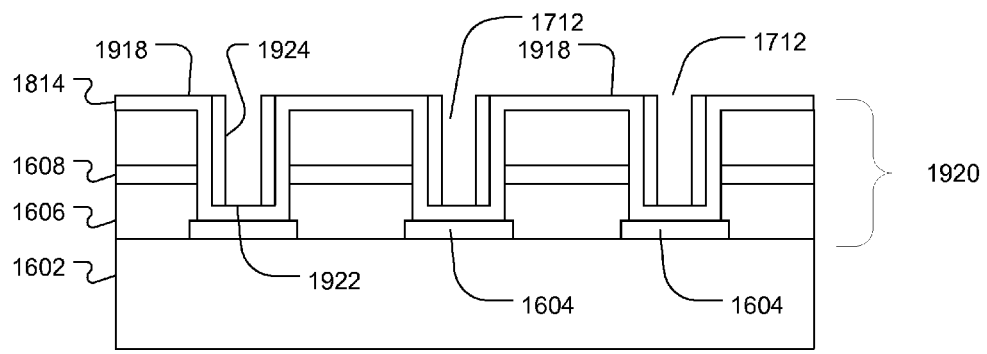

The silicon dioxide layer can be anisotropic etched to remove portions of the layer 1816 from the top surface of the well structure and the lower surface of the well, leaving portions of the layer 1816 on the well wall, as illustrated in FIG. 19. In addition, a wet etch can be used to strip an aluminum oxide layer, leaving an upper surface and a lower surface of exposed tantalum oxide. As a result, an upper surface 1918 of the well wall structure 1920 and a lower surface 1922 of the well 1712 include an exposed high intrinsic buffer capacity material, while a wall surface 1924 is defined by a low intrinsic buffer capacity oxide of silicon.

Figure 20:
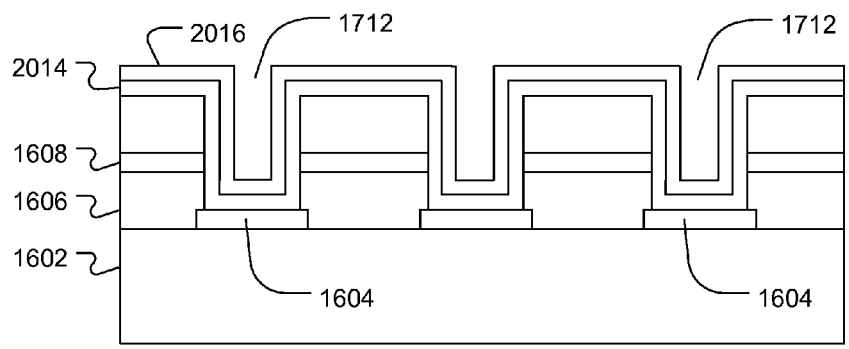

In another example, a well wall surface can be formed of a polymeric material, isolating high intrinsic buffer capacity materials from the well wall surface and limiting exposure of the high intrinsic buffer capacity materials to the upper surface of the well wall structure and a lower surface of the well. Returning to FIG. 17, a well 1712 is defined in one or more layers 1606, 1608, or 1610 to expose a sensor pad 1604. As illustrated in FIG. 20, one or more layers of high buffer capacity material can be deposited as a film 2014. For example, the film 2014 can include aluminum oxide, hafnium oxide, tantalum oxide, zirconium oxide, or a combination thereof. In a particular example, layers of aluminum oxide and tantalum oxide are deposited using atomic layer deposition. In the illustrated example, a layer of aluminum oxide is deposited over a layer of tantalum oxide, which is deposited over a further layer of aluminum oxide. A layer 2016 of an inorganic material, such as a polymeric material, is deposited over the film 2014. An exemplary polymeric material includes a polymer having an aromatic group in its backbone. For example, the polymer can be a poly(xylylene), such as a poly(p-xylylene), including functionalize p-xylylenes, such as halogenated p-xylylenes. In another example, the polymeric material includes a fluoropolymer. An exemplary fluoropolymer includes polytetrafluoroethylene (PTFE), polyvinylidene fluoride (PVDF), polyvinyl fluoride (PVF), fluorinated ethylene propylene (FEP) copolymer, ethylene chlorotrifluoroethylene (ECTFE) copolymer, a copolymer of tetrafluoroethylene, hexafluoropropylene, and vinylidene fluoride (THV), a copolymer of tetrafluoroethylene and perfluoro methylvinylether (PFA or MFA), a fluoropolymer having a fluorinated oxolane in its backbone, perfluoroether, or a combination thereof. In particular, the fluoropolymer can be a fluoropolymer having fluorinated oxolane in its backbone, for example, Cytop.

Figure 21:
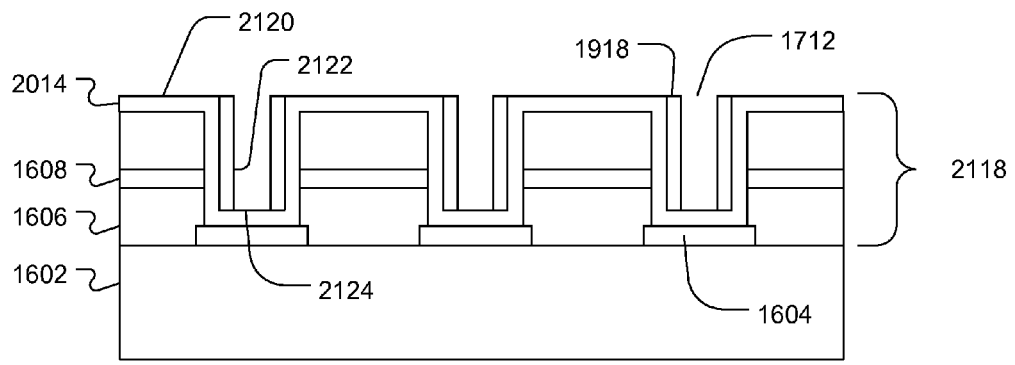

As illustrated in FIG. 21, the layer 2016 can be anisotropic wet etched to remove the polymer from an upper surface 2120 of the well wall structure 2118 and the lower surface 2124 of the well 1712. The polymeric material remains on the wall surface 2122 of the wells 1712. While not illustrated, a tantalum oxide layer can be exposed using a wet etch process to remove aluminum oxide. As a result, well wall structure 2118 includes an upper surface 2120 of exposed high intrinsic buffer capacity material, and lower surface 2124 of the well 1712 is defined by the same high intrinsic buffer capacity material. The layer 2016 of polymer forms the wall surface 2122 and isolates the well wall surface 2122 from the high intrinsic buffer capacity material of the film 2014.

Figure 22:
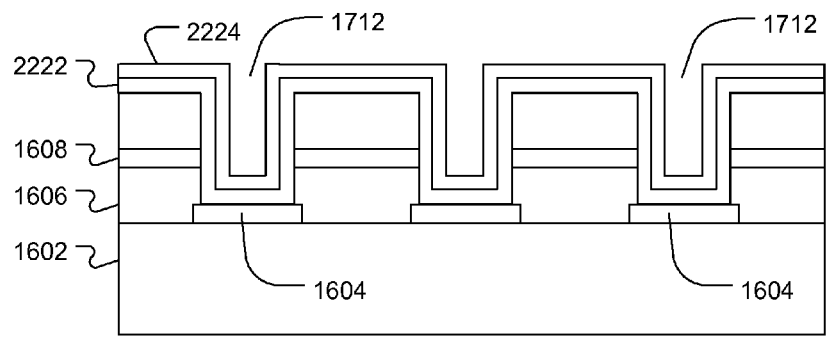

In a further example, the polymeric material can be substituted with an inorganic material, such as a nitride of silicon or titanium. In a particular material, the inorganic material is an electrically conductive material. Following from FIG. 17, FIG. 22 illustrates a film 2222 formed of one or more layers of high intrinsic buffer capacity material, such as aluminum oxide, hafnium oxide, tantalum oxide, zirconium oxide, or a combination thereof. The film 2222 can be formed as described above with the thicknesses described above. In a particular example, a three layer stack, including a layer of aluminum oxide over a layer of tantalum oxide, which is disposed over a layer of aluminum oxide, defines the film 2222. A layer 2224 of electrically conductive material is deposited over the film 2222. For example, the layer 2224 can be formed of a layer of titanium nitride.

Figure 23:
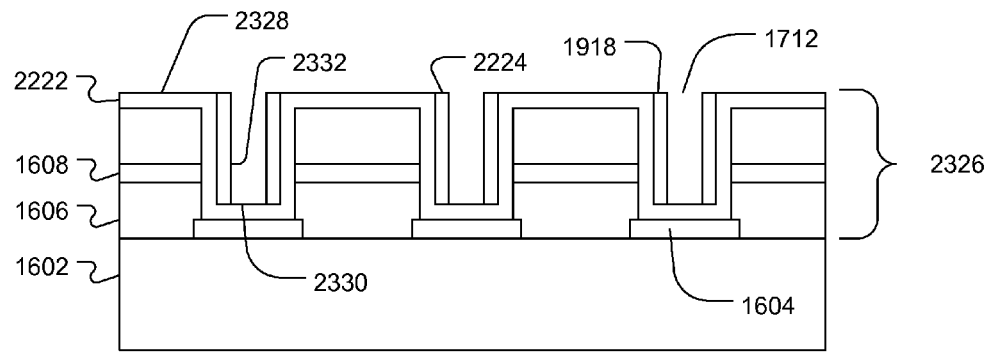

As illustrated in FIG. 23, the layer 2224 can be anisotropic wet etched to remove the electrically conductive film 2224 from a top surface 2328 of a well wall structure 2326 and a lower surface 2330 of the well 1712. The electrically conductive layer 2224 remains along a wall surface 2332. Further, an aluminum oxide layer of the film 2222 can be removed to expose a tantalum oxide layer on both the upper surface 2328 and the lower surface 2330.

Figure 24:
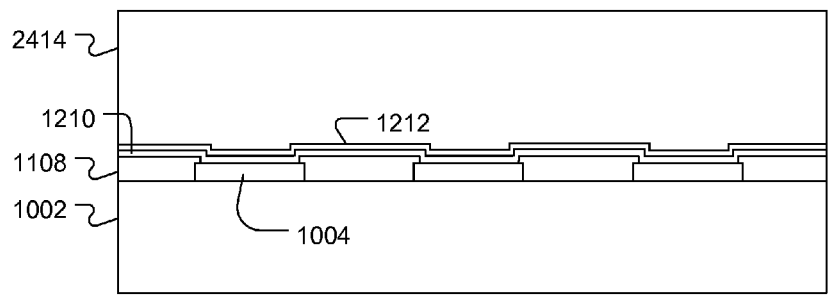

In a further embodiment, the well walls may be formed of a metallic material. In particular, the metal well walls can be formed using a process similar to a Damascene or dual-Damascene process. For example, following from FIG. 12, an oxide layer 2414 can be deposited over layers 1210 or 1212, as illustrated in FIG. 24. In particular, the layer 2414 is formed of a material that can be removed using a technique that will not damage or erode metallic layers or structures.

Figure 25:
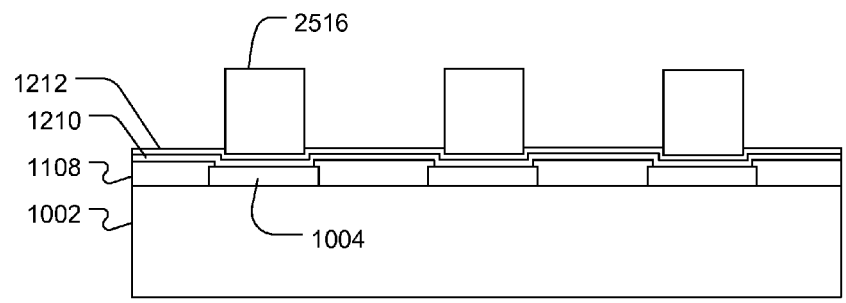

As illustrated in FIG. 25, the layer 2414 can be patterned using lithographic technique and etched to form well posts 2516. In particular, the well posts 2516 are disposed over the sensor pads 1004.

Figure 26:
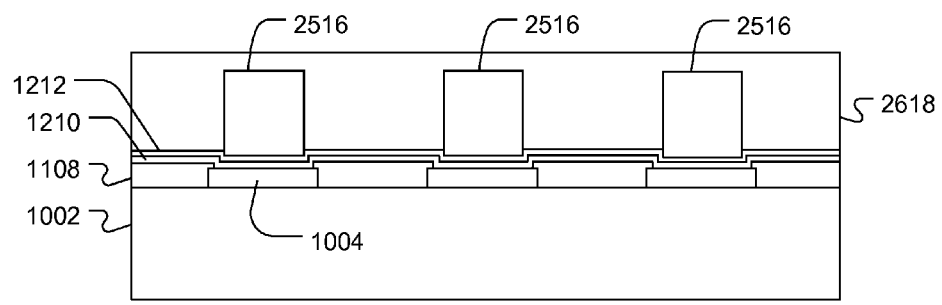

A metal layer 2618 can be deposited over the exposed layers 1210 or 1212, in addition to the well post 2516, as illustrated in FIG. 26. For example, the metal layer 2618 can be deposited using an electroplating technique. Alternatively, the metal layer 2618 can be deposited using liquid deposition techniques, sputtering, or evaporation techniques. The metal layer 2618 can be formed of a metal such as aluminum, copper, titanium, nickel, gold, silver, platinum or any combination thereof.

Figure 27:
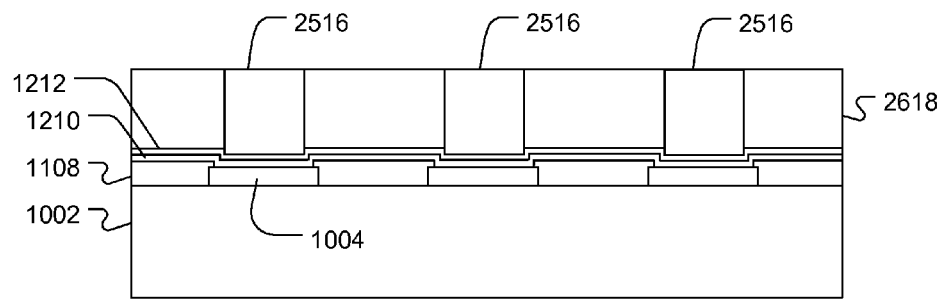

As illustrated in FIG. 27, the metal layer 2618 can be planarized to expose the well post 2516. For example, a chemical mechanical polishing technique can be utilized to planarize the metal layer 2618 and expose the well posts 2516.

Figure 28:
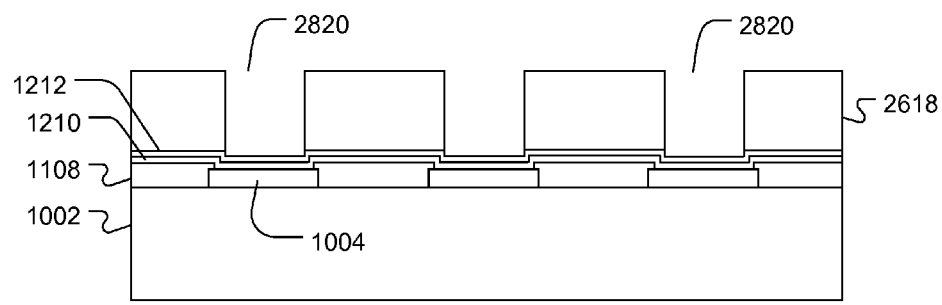

The well posts 2516 can be etched, for example, using a plasma etch technique, such as a reactive ion etch, to remove the well post 2516, leaving the metallic layer 2618 to define wells 2820, as illustrated in FIG. 28. While not illustrated, the aluminum oxide layer 1212 can be removed using a wet etch technique to expose the tantalum oxide layer 1210 over the sensor pad 1004.

Figure 29:
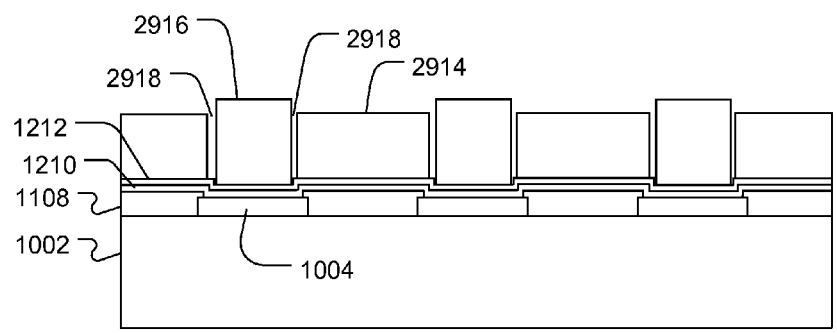

In an alternative example, ceramic materials can be used to support metallic layers that define the well wall. For example, following from FIG. 24, the layer 2414 can be etched in a pattern. In particular, the layer 2414 can be patterned using a lithographic technique and etched to form a trench 2918, as illustrated in FIG. 29. A well post 2916 is defined on an opposite side of the trench 2918 from a well wall structure 2914. In a particular example, the well post 2916 extends to a greater height over the CMOS structure 1002 than the well wall structure 2914.

Figure 30:
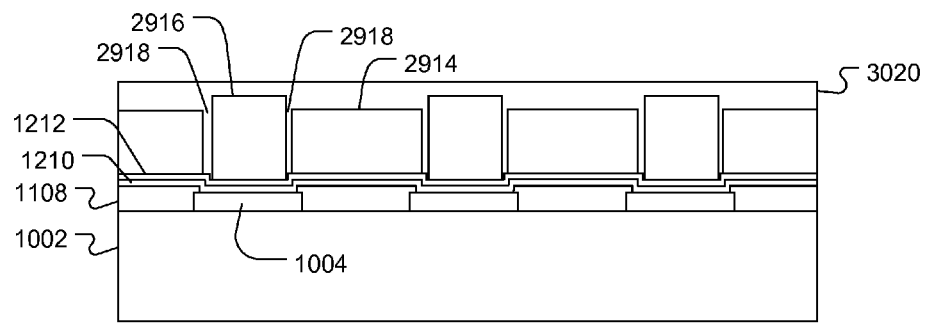

As illustrated in FIG. 30, a metal layer 3020 can be deposited over the well wall structure 2914 and the well post 2916 and within the trench 2918. For example, the metal layer 3020 be deposited using an electroplating technique. Alternatively, the metal layer can be deposited using liquid deposition techniques, sputtering, evaporation techniques, or a combination thereof. The metal layer 3020 can be formed of a metal such as aluminum, copper, nickel, gold, platinum, silver, titanium, or a combination thereof.

Figure 31:
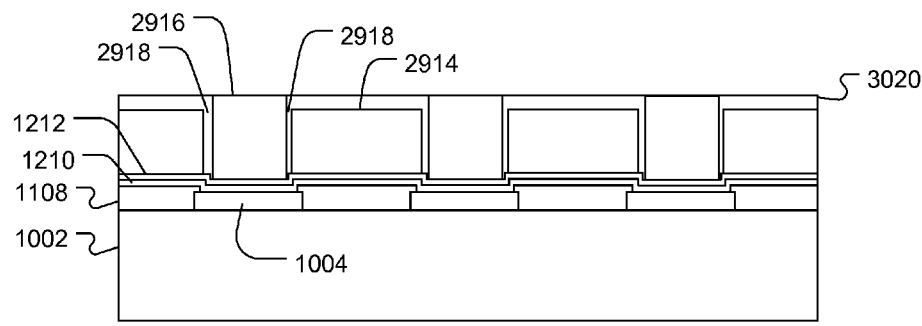
Figure 32:
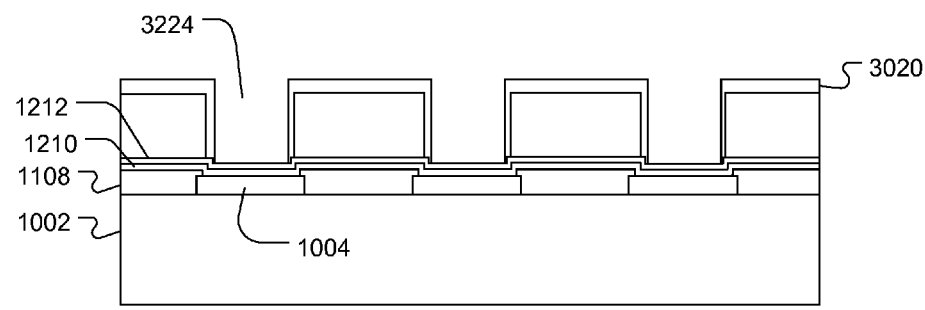

The metal layer 3020 can be planarized using, for example, chemical mechanical polishing to expose the well posts 2916, leaving a portion of the layer 3020 over the well wall structure 2914, as illustrated in FIG. 31. The well posts 2916 can be etched, removing the well posts 2916 and leaving wells 3224, as illustrated in FIG. 32. In addition, an aluminum oxide layer 1212 can be removed using a wet etch process to expose a tantalum oxide layer 1210 disposed over the sensor pad 1004.

Figure 33:
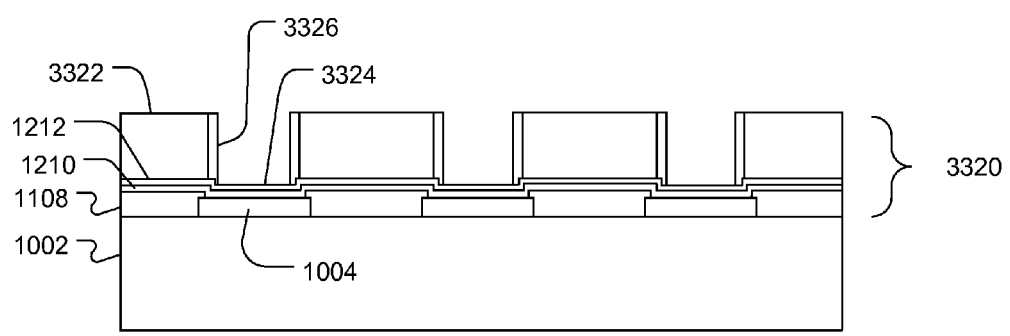

Optionally, an additional planarization process can be used to remove the metal layer 3020 from the upper surface 3322 of the well wall structure 3320, as illustrated in FIG. 33. As a result, the wall surface 3326 is defined by a metallic material, whereas the lower surface 3324 of the well 3224 is defined by high intrinsic buffer capacity material.

In each of the above embodiments in which a passivation layer, such as an oxide of tantalum, aluminum, hafnium, or zirconium, is disposed over the sensor pad and is exposed as part of the lower surface of a well, a coating such as those described above in relation to FIG. 3 can be used to enhance sensitivity of the system. Further, exposed upper surfaces of well wall structures can be enhanced with such coatings. In addition, coatings described above in relation to FIG. 3 that reduce the intrinsic buffer capacity of a surface can be used on the wall surfaces.

In a first aspect, a system includes a sensor including a sensor pad and a well wall structure defining a well operatively connected to the sensor pad. The sensor pad is associated with a lower surface of the well. The well wall structure defines an upper surface and a wall surface extending between the upper surface and the lower surface. The upper surface is defined by an upper buffer material having an intrinsic buffer capacity of at least $2 \times 10^{17}$ groups/m$^2$. The wall surface is defined by a wall material having an intrinsic buffer capacity of not greater than $1.7 \times 10^{17}$ groups/m$^2$.

In an example of the first aspect, the upper buffer material has an intrinsic buffer capacity of at least $4 \times 10^{17}$ groups/m$^2$. For example, the upper buffer material can have an intrinsic buffer capacity of at least $8 \times 10^{17}$ groups/m$^2$, such as an intrinsic buffer capacity of at least $1 \times 10^{18}$ groups/m$^2$, or at least $2 \times 10^{18}$ groups/m$^2$. In a particular example of the first aspect, the upper buffer material has an intrinsic buffer capacity of not greater than $1 \times 10^{21}$ groups/m$^2$.

In another example of the first aspect or the above examples, the wall material has an intrinsic buffer capacity of not greater than $1 \times 10^{17}$ groups/m$^2$. For example, the wall material has an intrinsic buffer capacity of not greater than $5 \times 10^{16}$ groups/m$^2$, such as an intrinsic buffer capacity of not greater than $2 \times 10^{16}$ groups/m$^2$, not greater than $1 \times 10^{16}$ groups/m$^2$, or not greater than $5 \times 10^{15}$ groups/m$^2$.

In a further example of the first aspect or the above example, the lower surface of the well is defined by a lower buffer material disposed over the sensor pad. In an additional example of the first aspect or the above examples, the lower buffer material has an intrinsic buffer capacity of at least $2 \times 10^{17}$ groups/m$^2$, such as an intrinsic buffer capacity of at least $4 \times 10^{17}$ groups/m$^2$, at least $1 \times 10^{18}$ groups/m$^2$, or at least $2 \times 10^{18}$ groups/m$^2$. In another example of the first aspect or the above examples, the lower buffer material has an intrinsic buffer capacity of not greater than $1 \times 10^{21}$ groups/m$^2$. In a further example of the first aspect or the above examples, the upper buffer material and the lower buffer material are the same.

In an additional example of the first aspect, the upper buffer material includes an inorganic material.

In another example of the first aspect or the above examples, the upper buffer material includes a ceramic material. In a particular example, the ceramic material includes an oxide of aluminum, hafnium, tantalum, zirconium, or a combination thereof. For example, the ceramic material includes an oxide of tantalum. In another example, the ceramic material includes an oxide of aluminum.

In a further example of the first aspect or the above examples, the wall material includes an inorganic material. For example, the inorganic material includes a ceramic material. In an example, the ceramic material includes a nitride of silica or titanium. In another example, the ceramic material includes an oxide of silicon. In a further aspect, the inorganic material includes a metal material. For example, the metal material includes aluminum, copper, nickel, titanium, gold, silver, platinum, or a combination thereof. In a particular example, the metal material includes copper.

In an additional example of the first aspect or the above examples, the wall material includes an organic material. For example, the organic material includes a polymeric material. In an example, the polymeric material includes poly(xylylene).

In another example of the first aspect or the above examples, the sensor and wall structure are integral to an electronic component. For example, the electronic component is disposed in cooperation with a flow chamber to place the sensor and the well wall structure in fluid communication with an aqueous solution. In another example, the electronic component is in signal communication with a processor.

In a second aspect, a method of forming a sensor system includes forming a structural layer over a sensor device. The sensor device includes a sensor pad. The structural layer includes a structural material having an intrinsic buffer capacity of not greater than $1.7 \times 10^{17}$ groups/m$^2$. The method further includes forming a buffer layer over the structural layer. The buffer layer includes a buffer material having an intrinsic buffer capacity of at least $2 \times 10^{17}$ groups/m$^2$. The method also includes etching the buffer layer and the structural layer to define a well operatively connected to the sensor pad.

In an example of the second aspect, the structural material has an intrinsic buffer capacity of not greater than $1 \times 10^{17}$ groups/m$^2$. For example, the buffer material has an intrinsic buffer capacity of at least $4 \times 10^{17}$ groups/m$^2$.

In another example of the second aspect or the above examples, the method further includes forming a passivation layer over the sensor pad prior to forming the structural layer, the passivation layer disposed between the sensor device and the structural layer. In a further example, the method further includes forming an etch stop layer over the passivation layer. The etch stop layer is disposed between the structural layer and the passivation layer. For example, etching can include exposing the passivation layer.

In an additional example of the second aspect or the above examples, forming the structural layer includes forming a first dielectric layer and forming a second dielectric layer, a material of the first dielectric layer being different from a material of the second dielectric layer. For example, the method can further include forming a third dielectric layer over the second dielectric layer, a material of the second dielectric layer being different from a material of the third dielectric layer. In particular, the first dielectric layer can include an oxide of silicon. In another example, the second dielectric layer can include silicon nitride. In a further example of the second aspect or the above examples, forming the structural layer includes depositing TEOS.

In a third aspect, a method of sequencing a polynucleotide includes applying a particle comprising a plurality of copies of a polynucleotide to a well of a system of the first aspect, exposing the particle to an aqueous solution including a nucleotide, and measuring a response of the device to the exposing.

In a fourth aspect, a system includes a sensor device including a sensor pad and a well wall structure defining a well in operative connection with the sensor pad. A lower surface of the well is defined over the sensor pad. The well wall structure has an upper surface and a wall surface extending between the upper surface and the lower surface. The system includes a passivation film disposed over the upper surface, the wall surface and the lower surface and an isolation film disposed over the passivation film opposite the well wall structure and extending substantially parallel to and at least along a portion of the wall surface. The passivation layer is exposed at least along a portion of the upper surface and at least along a portion of the lower surface.

In an example of the fourth aspect, the passivation layer includes a buffer material having an intrinsic buffer capacity of at least $2 \times 10^{17}$ groups/m$^2$. In another example of the fourth aspect or the above examples, the buffer material includes an oxide of zirconium, aluminum, tantalum, hafnium, or a combination thereof. In an additional example of the fourth aspect or the above examples, the buffer material includes an oxide of tantalum.

In another example of the fourth aspect or the above examples, the isolation layer includes a low buffer material having an intrinsic buffer capacity of not greater than $1.7 \times 10^{17}$ groups/m$^2$. In an additional example of the fourth aspect or the above examples, the low buffer material includes a ceramic material. For example, the low buffer material includes an oxide of silicon. In an example, the low buffer material includes a nitride of silicon, titanium, or a combination thereof. In an additional example of the fourth aspect or the above examples, the low buffer material includes a polymeric material. For example, the polymeric material include poly(xylylene).

In a fifth aspect, a method of forming a sensor system includes forming a structural layer over a sensor device, the sensor device including a sensor pad and etching the structural layer to define a well operatively connected to the sensor pad. A lower surface of the well is defined over the sensor pad. The structurally layer has an upper surface and a wall surface extending between the upper surface and the lower surface. The method includes forming a passivation film over the structural layer. The passivation film extends along at least a portion of the upper surface and extends over the wall surface and the lower surface. The method further includes forming an isolation film over the passivation film and etching the isolation film to expose the passivation film along at least the portion of the upper surface and at least a portion of the lower surface.

In an example of the fifth aspect, forming the structural layer includes forming a first dielectric layer and forming a second dielectric layer, a material of the first dielectric layer being different from a material of the second dielectric layer.

In another example of the fifth aspect or the above examples, the method further includes forming a third dielectric layer over the second dielectric layer, a material of the second dielectric layer being different from a material of the third dielectric layer.

In an additional example of the fifth aspect or the above examples, the first dielectric layer includes an oxide of silicon. In another example, the second dielectric layer includes silicon nitride.

In a further example of the fifth aspect or the above examples, forming the structural layer includes depositing TEOS.

In an example of the fifth aspect or the above examples, forming the passivation layer includes depositing a buffer material having an intrinsic buffer capacity of at least $2\times10^{17}$ groups/m$^2$.

In another example of the fifth aspect or the above examples, forming the passivation layer includes depositing an oxide of aluminum, zirconium, hafnium, tantalum, or a combination thereof.

In an additional example of the fifth aspect or the above examples, forming the isolation layer includes depositing an inorganic material. In an example, the inorganic material includes a nitride of titanium, silicon, or a combination thereof.

In a further example of the fifth aspect or the above examples, forming the isolation layer includes depositing a polymeric material. In an example, the polymeric material includes a poly(xylylene).

In another example of the fifth aspect or the above examples, etching the isolation material includes anisotropic etching the isolation material.

In a sixth aspect, a method of sequencing a polynucleotide includes applying a particle comprising a plurality of copies of a polynucleotide to a well of a system of the fourth aspect, exposing the particle to an aqueous solution including a nucleotide, and measuring a response of the device to the exposing.

In a seventh aspect, a system includes a sensor device including a sensor pad and a well wall structure defining a well in operative connection with the sensor pad. A lower surface of the well is defined over the sensor pad. The well wall structure has an upper surface, and a wall surface extends between the upper surface and the lower surface. A metal layer is disposed over the well wall structure and extends along the upper surface and the wall surface.

In an example of the seventh aspect, the metal layer includes aluminum, copper, nickel, gold, silver, titanium, platinum, or a combination thereof. For example, the metal layer can include copper. In a further example, the lower surface is free of the metal layer.

In another example of the seventh aspect or the above examples, the wall surface extends substantially vertically.

In a further example of the seventh aspect or the above examples, the well wall structure includes an inorganic material. In another example, the inorganic material includes a ceramic material. For example, the ceramic material includes a nitride of silica or titanium. In another example, the ceramic material includes an oxide of silicon.

In an eighth aspect, a method of forming a sensor system includes forming a structural layer over a sensor device, the sensor device including a sensor pad, and etching the structural layer to form a trench defining a well post over the sensor pad and a well wall structure opposite the first structure, the well post extending vertically higher than the well wall structure. The method further includes depositing a metal layer into the trench and over the well post and the well wall structure, exposing the well post, and etching to remove the well post.

In a ninth aspect, a method of forming a sensor system includes forming a structural layer over a sensor device, the sensor device including a sensor pad, etching the structural layer to form a well post over the sensor pad, depositing a metal layer to surround the well post, and etching to remove the well post.

In a tenth aspect, a method of sequencing a polynucleotide includes applying a particle comprising a plurality of copies of a polynucleotide to a well of a system of the seventh aspect, exposing the particle to an aqueous solution including a nucleotide, and measuring a response of the device to the exposing.

As used herein, the terms "over" or "overlie" refers to a position away from a surface relative to a normal direction from the surface. The terms "over" or "overlie" are intended to permit intervening layers or direct contact with an underlying layer. As described above, layers that are disposed over or overlie another layer can be in direct contact with the identified layer or can include intervening layers.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and FIG.s are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A system comprising:
    a sensor including a sensor pad; and
    a well wall structure defining a well operatively connected to the sensor pad, the sensor pad associated with a lower surface of the well, the well wall structure defining an upper surface and a wall surface extending between the upper surface and the lower surface, the upper surface defined by an upper buffer material having an intrinsic buffer capacity of at least $2\times10^{17}$ groups/m$^2$ and not greater than $1\times10^{21}$ groups/m$^2$, the wall surface being defined by a wall material having an intrinsic buffer capacity of not greater than $1.7\times10^{17}$ groups/m$^2$.

2. The system of claim 1, wherein the upper buffer material has an intrinsic buffer capacity of at least $4\times10^{17}$ groups/m$^2$.

3. The system of claim 1, wherein the lower surface of the well is defined by a lower buffer material disposed over the sensor pad.

4. The system of claim 3, wherein the lower buffer material has an intrinsic buffer capacity of at least $2\times10^{17}$ groups/m$^2$.

5. The system of claim 3, wherein the upper buffer material and the lower buffer material are the same.

6. The system of claim 1, wherein the upper buffer material includes an inorganic material.

7. The system of claim 1, wherein the upper buffer material includes a ceramic material.

8. The system of claim 7, wherein the ceramic material includes an oxide of aluminum, hafnium, tantalum, zirconium, or a combination thereof.

9. The system of claim 1, wherein the wall material includes an inorganic material.

10. The system of claim 9, wherein the inorganic material includes a ceramic material.

11. The system of claim 10, wherein the ceramic material includes a nitride of silica or titanium.

12. The system of claim 10, wherein the ceramic material includes an oxide of silicon.

13. The system of claim 9, wherein the inorganic material includes a metal material.

14. The system of claim 1, wherein the wall material includes an organic material.

15. The system of claim 14, wherein the organic material includes a polymeric material.

16. The system of claim 1, wherein the sensor and wall structure are integral to an electronic component.

17. The system of claim 16, wherein the electronic component is disposed in cooperation with a flow chamber to place the sensor and the well wall structure in fluid communication with an aqueous solution.

18. A method of forming a sensor system, the method comprising:

forming a structural layer over a sensor device, the sensor device including a sensor pad, the structural layer including a structural material having an intrinsic buffer capacity of not greater than $1.7\times10^{17}$ groups/m$^2$;

forming a buffer layer over the structural layer, the buffer layer including a buffer material having an intrinsic buffer capacity of at least $2\times10^{17}$ groups/m$^2$ and not greater than $1\times10^{21}$ groups/m$^2$; and etching the buffer layer and the structural layer to define a well operatively connected to the sensor pad.

19. The method of claim 18, wherein the structural material has an intrinsic buffer capacity of not greater than $1\times10^{17}$ groups/m$^2$.

20. The method of claim 18, wherein the buffer material has an intrinsic buffer capacity of at least $4\times10^{17}$ groups/m$^2$.

21. The method of claim 18, further comprising forming a passivation layer over the sensor pad prior to forming the structural layer, the passivation layer disposed between the sensor device and the structural layer.

22. The method of claim 18, wherein forming the structural layer includes forming a first dielectric layer and forming a second dielectric layer, a material of the first dielectric layer being different from a material of the second dielectric layer.

23. The method of claim 22, further comprising forming a third dielectric layer over the second dielectric layer, a material of the second dielectric layer being different from a material of the third dielectric layer.

24. A method of sequencing a polynucleotide, the method comprising:

applying a particle comprising a plurality of copies of a polynucleotide to a well of a system comprising:
  a sensor including a sensor pad; and
  a well wall structure defining a well operatively connected to the sensor pad, the sensor pad associated with a lower surface of the well, the well wall structure defining an upper surface and a wall surface extending between the upper surface and the lower surface, the upper surface defined by an upper buffer material having an intrinsic buffer capacity of at least $2\times10^{17}$ groups/m$^2$ and not greater than $1\times10^{21}$ groups/m$^2$, the wall surface being defined by a wall material having an intrinsic buffer capacity of not greater than $1.7\times10^{17}$ groups/m$^2$;

exposing the particle to an aqueous solution including a nucleotide; and measuring a response of the device to the exposing.

* * * * *